United States Patent [19]
Martz et al.

[11] Patent Number: 5,145,364
[45] Date of Patent: Sep. 8, 1992

[54] REMOVABLE ORTHODONTIC APPLIANCE

[75] Inventors: Martin G. Martz, Bakersfield, Calif.; Robert D. Brining, Aspen, Colo.

[73] Assignee: M-B Orthodontics, Inc., Aspen, Colo.

[21] Appl. No.: 700,775

[22] Filed: May 15, 1991

[51] Int. Cl.[5] .............................................. A61C 3/00
[52] U.S. Cl. ............................................... 433/6; 433/18
[58] Field of Search ................. 433/6, 10, 11, 18, 19, 433/20, 21, 22

[56] References Cited

U.S. PATENT DOCUMENTS

| | | | |
|---|---|---|---|
| 3,510,946 | 5/1970 | Kesling | 433/6 |
| 3,724,075 | 4/1973 | Kesling | 433/6 |
| 3,837,081 | 9/1974 | Kesling | 433/6 |
| 4,139,944 | 2/1979 | Bergersen | 433/6 |
| 4,273,530 | 6/1981 | Broussard | 433/6 |
| 4,505,672 | 3/1985 | Kurz | 433/6 |
| 4,708,646 | 11/1987 | Jasper | 433/19 |
| 4,755,139 | 7/1988 | Abatte | 433/6 |
| 4,793,803 | 12/1988 | Martz | 433/6 |
| 4,798,534 | 1/1989 | Breads | 433/6 |
| 4,856,991 | 8/1989 | Breads | 433/6 |
| 4,880,380 | 11/1989 | Martz | 433/11 |

OTHER PUBLICATIONS

Zahnarztliche Rundschau Dreibigjahrige (etc), Herbst Sep. 1934.
Dental Record, Demonstrations Adams May 1950.
The Description Constraction of Removable Orthodontic Appliances, Adams 1964 pp. 44-49.

*Primary Examiner*—Cary E. O'Connor
*Attorney, Agent, or Firm*—Julian Caplan

[57] ABSTRACT

Dental clasps are removable secured to teeth in part by wire ears engaging the natural undercut of the teeth and in part by engagement with buttons adhered to the teeth. Clasps are modified for the above purpose and also form combinations to engage different areas of teeth to correct various occlusions. Preferably the clasps are encased in molded plastic appliances which fit a single arch or a portion thereof or fit both arches. The plastic appliance preferably does not cover the occlusal surfaces; hence the patient's mouth may close to a more normal position. The buttons are shaped to facilitate installation of the appliance, as by tapering the outside surface of the button or the slot in the button which receives the clasp.

46 Claims, 20 Drawing Sheets

PRIOR ART

Figure 11
Figure 10
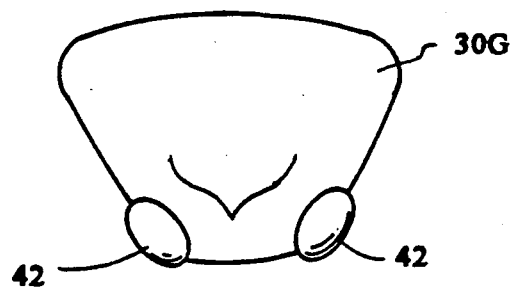
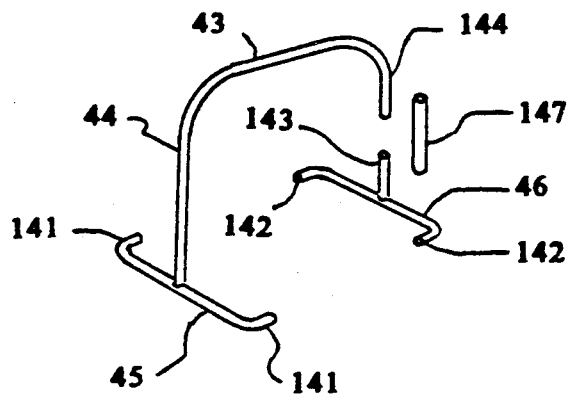
Figure 11A
Figure 12
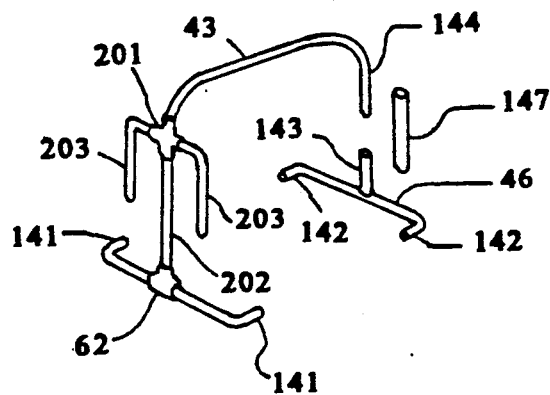
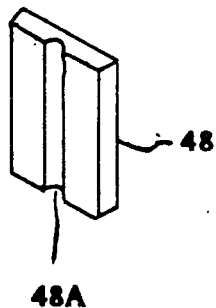
Figure 12A
Figure 12B
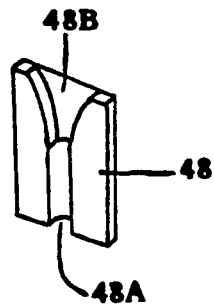
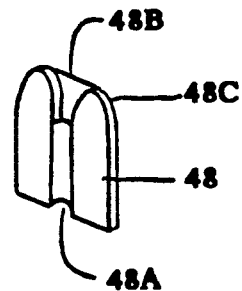

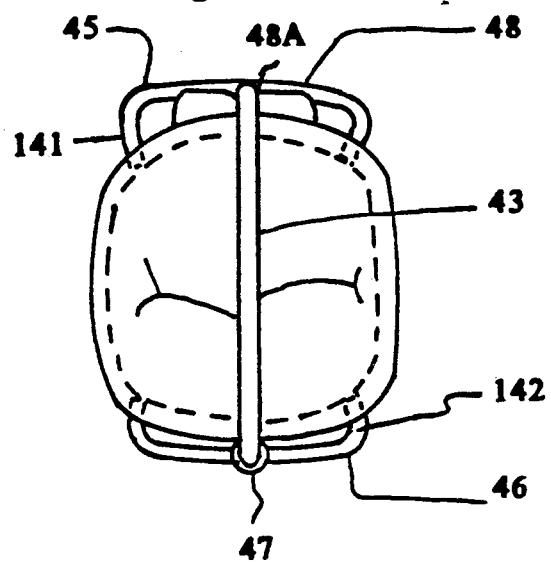
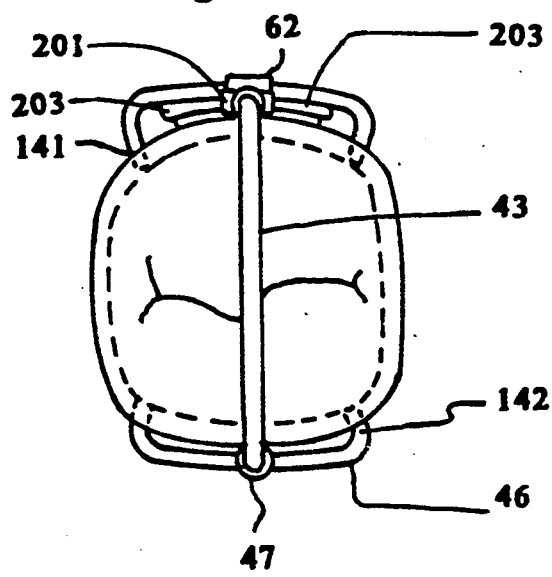

Figure 42
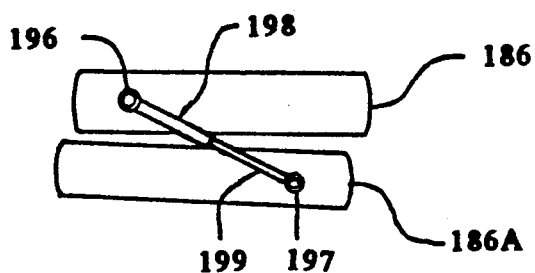
Figure 42A
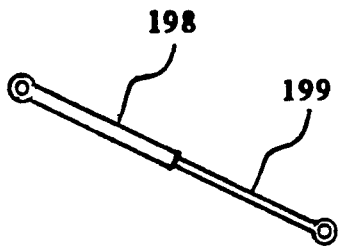
Figure 42B
Figure 43
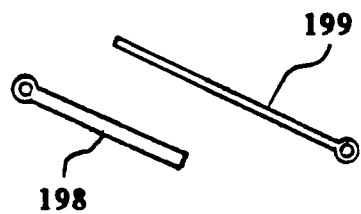
Figure 43A
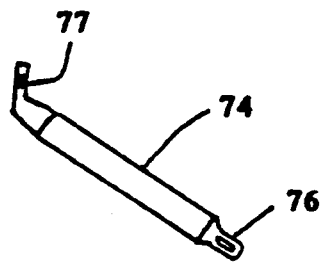
Figure 44
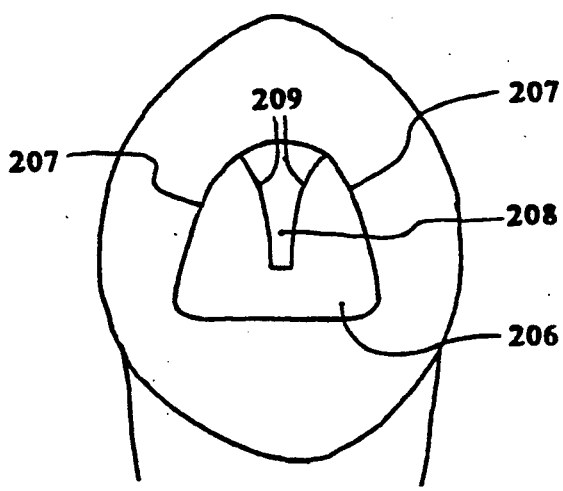

REMOVABLE ORTHODONTIC APPLIANCE

BACKGROUND OF THE INVENTION

1. Field of the Invention

This invention relates to a new and improved removable orthodontic appliance, and more particularly relates to orthodontic appliances wherein dental clasps of a type used for many years are modified. One means of modification is the use of buttons affixed to one or more surfaces of teeth which cooperate with the clasps to aid in correcting various types of malocclusions. The buttons may be shaped to facilitate installation of an appliance as by tapering the outside surfaces of the buttons or tapering the slot in the button which receives a portion of the clasp. Preferably the clasps are encased in molded, flexible appliances of silicone rubber, plastic or other suitable material hereinafter referred to as "flexible material" which fit a single arch or a portion thereof or fit both arches. The flexible material may cover the occlusal surfaces but preferably do not cover the occlusal surfaces, making it possible for the patient to close his mouth to a more normal position.

2. Description of Related Art

One of the important elements of the combination hereinafter described in detail is an Adams clasp which has been used in dentistry for many years. Such a clasp is formed of spring wire and engages the facial and/or lingual surfaces of the teeth, preferably engaging undercuts of the tooth. In accordance with the present invention, however, the Adams clasp is modified in structure and preferably is used in conjunction with molded, resilient flexible material appliances which encase the clasps and are molded to fit one or both arches of the patient The coverings augment the clasps, biasing the teeth into normal position.

Patents and articles of Kesling disclose appliances of resilient material which engage the upper and lower arches of the patient to modify certain types of occlusions. The present invention is an improvement thereon in the sense that the clasps heretofore mentioned provide a more positive engagement on the patient's teeth and hence are more effective in modifying occlusions.

Martz U.S. Pat. Nos. 4,793,803 and 4,880,380 disclose appliances which are intended for the same purpose as the present invention, and also disclose buttons which are adhered to the teeth of the patient. However, the combination of such appliances and buttons with the clasps hereinafter described in detail is novel.

Appliances which affect the relative positions of the upper and lower arches are disclosed in Jasper U.S. Pat. No. 4,708,646 and in journals authored by Herbst. Modifications of these disclosures are employed in the present invention but only in combination with details heretofore set forth.

Kurz U.S. Pat. No. 4,505,672 discloses upper and lower positioners having guideways, which are not used in the present invention.

Abbatte U.S. Pat. No. 4,755,139 discloses repositioning anterior teeth of a first jaw by installing a hard splint on the opposite jaw and using an elastic joined to the splint to urge the anterior teeth.

SUMMARY OF THE INVENTION

The prior art Adams clasp has been manufactured in a number of variations. Essentially it is made of spring wire and can engage undercuts of either the facial or lingual surfaces of the tooth. Additionally, the use of buttons engaged by appliances is disclosed in Martz U.S. Pat. No. 4,793,803. In accordance with the present invention, in order to more effectively secure the Adams-type clasp to tooth surfaces where an undercut is not present or is present only to a minor degree, the clasp is formed in such manner that it is held on the tooth by a button adhered thereto.

As disclosed herein, the clasp may be of a variety of shapes to engage different tooth surfaces and to correct various malocclusions. The various modifications of the invention are set forth in detail in the accompanying drawings and description of preferred embodiments.

As shown in Martz U.S. Pat. No. 4,793,803, molded, resilient flexible material conforms to the arches of individual patients and biases the individual teeth to correct malocclusions. In accordance with the present invention, however, the appliances are formed of a molded, flexible material which covers portions of one or both arches and encases the clasps and buttons heretofore mentioned. Such appliances may be unitary in that they fit both arches or they may fit a single arch. Where the appliances fit single arches, they may be interconnected by so-called Jasper jumpers or Herbst connectors or elastics to move one arch relative to the other. Individual appliances may cover the occlusal surfaces of the arch or the occlusal surfaces may be uncovered. In the latter instance, the patient is able to close his jaws in a more normal fashion.

An important feature of the invention is that the appliances may be removed and reinstalled by the patient as required as, for example, when eating. The buttons adhered to the tooth are so shaped as to facilitate reinstallation of the appliances.

DESCRIPTION OF DRAWINGS

The accompanying drawings, which are incorporated in and form a part of this specification, illustrate embodiments of the invention and, together with the description, serve to explain the principles of the invention:

FIG. 10 is an occlusal view of the structure of FIG. 9.

FIG. 11 is an exploded perspective view of another clasp.

FIG. 11A is a view similar to FIG. 11 of a modified clasp.

FIG. 12 is a perspective view of a button used in accordance with the invention.

FIG. 12A and FIG. 12B are perspective views similar to FIG. 12 showing modifications of the button of FIG. 12.

FIG. 14 is an occlusal view of the clasp of FIG. 13.

FIG. 14A is a view similar to FIG. 14 showing use of the clasp of FIG. 11A.

FIG. 42 is a view similar to FIG. 41 showing Herbst telescoping arms.

FIG. 42A is an enlarged elevational view of the Herbst appliance.

FIG. 42B is an enlarged elevational view showing the appliance disassembled.

FIG. 43 is a view similar to FIG. 41 showing use of a Jasper jumper FIG. 43A is a side elevational view of the jumper of FIG. 43.

FIG. 44 is an elevational view showing the facial surface of a lower bicuspid, with a button bonded to it.

DESCRIPTION OF PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
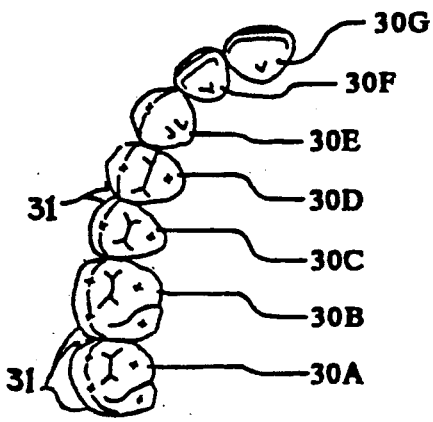
FIG. 1 is a top plan view of a portion of a dental arch having arrows indicating the undercut areas of normal teeth.
Figure 3:
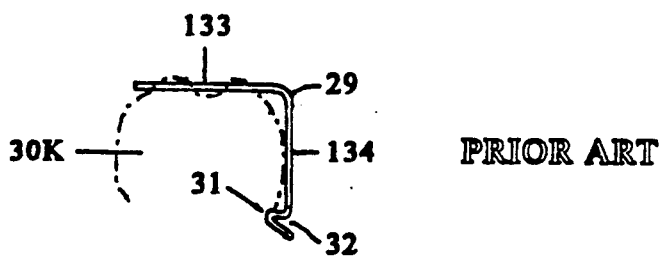
FIG. 3 is a side elevation of the structure of FIG. 2.
Figure 4:
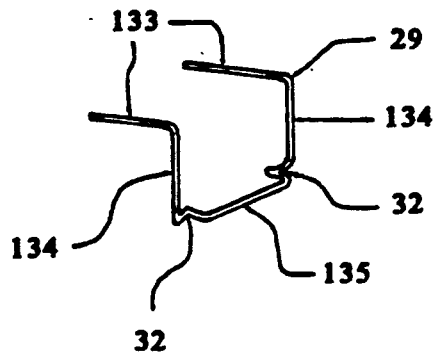
FIG. 4 is a perspective view of a conventional Adams clasp.
Figure 5:
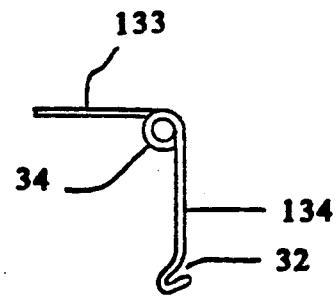
FIGS. 5 and 5A show modified Adams clasps.
Figure 5A:
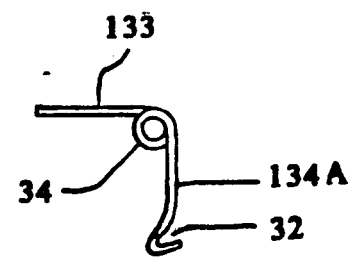

FIG. 1 shows an occlusal view of a portion of a dental arch comprising teeth 30a, b, c, etc. The locations of natural undercuts 31 are indicated by short arrows. Generally speaking, anterior teeth do not have significant natural undercuts above the gum line when normally oriented. In accordance with the prior art, Adams clasps 29 have been used in orthodontia and are formed with bent wire "ears" 32 to engage undercuts 31. Thus, as best shown in FIGS. 3 and 4, the clasp 29 has pair of generally horizontal stretches 133 fitting over the occlusal surface of tooth 30k and a vertical stretch 134, each of which terminates in ear 32 and the opposed ears 32 are interconnected by a horizontal stretch 135. FIGS. 5 and 5A show modifications of the structure shown in FIG. 3 wherein coils 34 are formed at the intersections of the stretches 133 and 134. The vertical dimensions 134 and 134a accommodate teeth of different size. Adding a coil 34 provides greater flexibility to the clasp and thereby allows the use of heavier wire which is not so readily damaged inadvertently by the wearer. The coil 34 adds bulk and complexity in fabrication and also makes adjustment more difficult. Heretofore, such coils have not been used. The present invention encompasses the uses of such coils in many instances.

Figure 2:
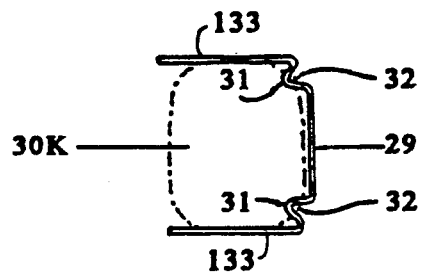
FIG. 2 is a top plan view showing an Adams clasp applied to a molar.
Figure 6:
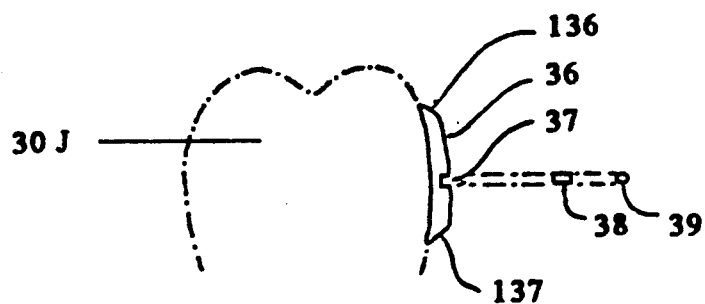
FIG. 6 is a side elevational view of a tooth showing a button adhered thereto.
Figure 7:
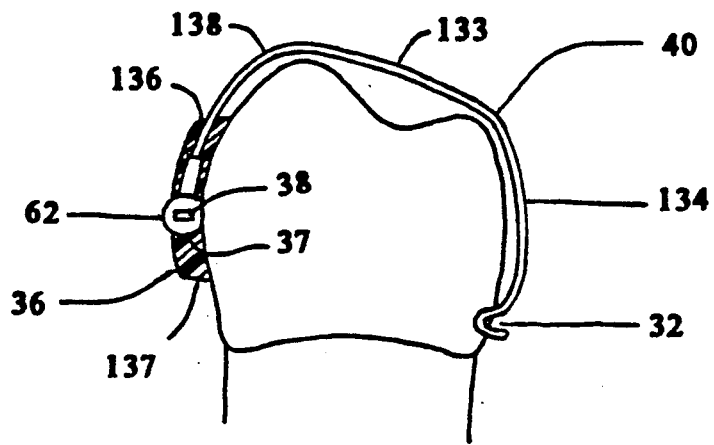
FIG. 7 is a side elevational view showing use of an Adams clasp and a button in accordance with the present invention.
Figure 8:
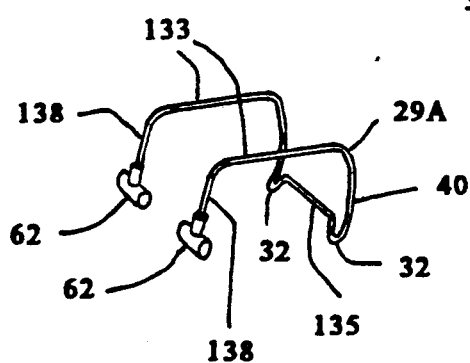
FIG. 8 is a perspective view showing a modified clasp.
Figure 8A:
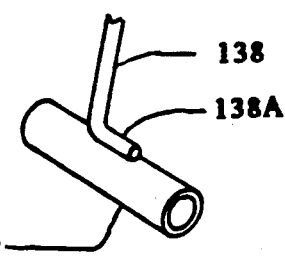
FIG. 8A is an enlarged perspective view of a modified method of attaching a wire to a tube.

FIG. 6 is a side view of a low-profile button 36 formed with a rectangular cross-sectional horizontal slot 37 which receives a wire such as the rectangular cross-sectional wire 38 or the round cross-sectional wire 39. The upper and lower edges 136, 137 of button 36 are rounded to allow the wire or clasp to slide more easily over the button. The edges of slot 37 are rounded above and below to guide archwires 38 or 39 into the slot. As shown in FIG. 6, button 36 is applied to the facial surface of tooth 30j. As best shown in FIG. 8, the Adams clasp 29a shown therein differs from the clasp of FIGS. 2-4 in that there are downward extending forward vertical stretches 138 at the facial ends of stretches 133 which terminate in Tees 62. As shown in FIGS. 8 and 7, the Tees 62 are inverted and the vertical arms thereof receive the lower ends of the stretches 138 and are crimped thereto. Alternatively a tube may be soldered, welded or cemented to the ends of stretches 138 to hold the archwire 39, as is shown in FIG. 8A. The end of stretch 138 may be bent to facilitate attachment of the tube. An archwire 39 passes through the bottom legs of the Tees 62 or tubing 139. The facial side of the tooth has a button 36 bonded thereto. The clasp assembly 40 is made from a continuous piece of wrought spring wire with ears 32 bent into it forming a modification of an Adams clasp to grip the lingual side of the tooth. The ends of the vertical stretch wires 138 are inserted into the Tee-shaped tubes 62 on the facial side to hold the archwire 39, which in turn is inserted into the horizontal slot 37 of button 36 as well as through the horizontal passageways of Tees 62 or tubes 139.

Figure 7A:
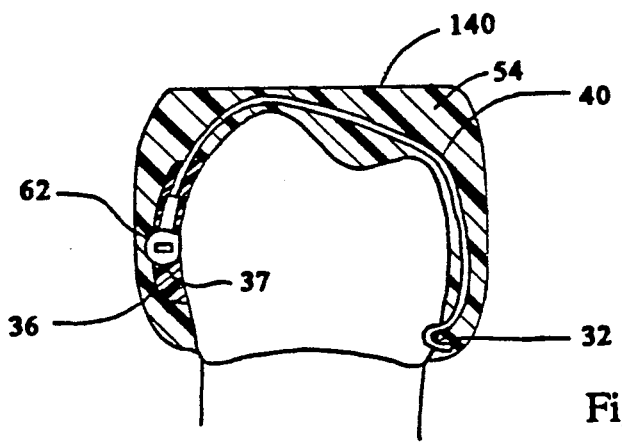
FIG. 7A shows the structure of FIG. 7 enclosed in a casing covering the occlusal tooth surface.

FIG. 7A is a side view of the same tooth as shown in FIG. 7 and the same button and archwire applied thereto. This figure shows a cross-section of a full-coverage appliance 54 made to fit over a single dental arch, as more completely shown in FIG. 35. The arrow 140 indicates a flat occlusal surface of the molded flexible material 54 which flows around and envelops the clasp assembly which includes the clasp 40. The surface 140 may be of a harder material, whereas the remaining appliance 54 may be more resilient in order to bias the tooth to normal position. See U.S. Pat. No. 4,793,803 for a description of how an appliance having a tooth engaging portion, a stiff backbone and an intermediate resilient position may function for such purpose.

Figure 7B:
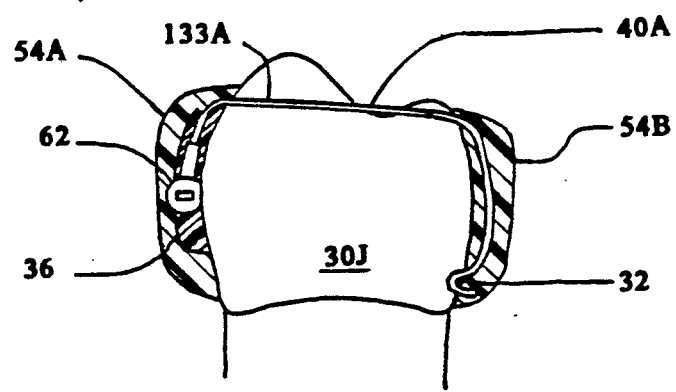
FIG. 7B is a view similar to FIG. 7A showing a modification wherein the casing does not cover the occlusal surface.
Figure 34:
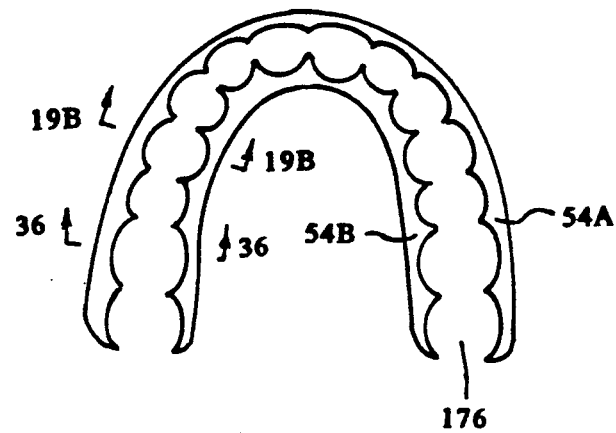
FIG. 34 is an occlusal view of a partial coverage appliance.

FIG. 7B is a side view of the tooth of FIG. 7 showing a cross-section of a partial-coverage appliance comprising parts 54a, 54b made to fit over a single dental arch, as more specifically set forth in FIG. 34. The wrought clasp 40a is shaped differently than in FIG. 7A or 7 in that the horizontal stretch 133a is flat and does not extend above the height of the cusps of tooth 30a. The horizontal stretches 133a extend over the marginal ridges of the teeth only and not over the cusps. The molded flexible appliance is in two pieces, a facial piece 54a and a lingual piece 54b. The partial coverage appliance may be used alone on one dental arch or may be used when the other opposing dental arch has a similar partial-coverage appliance or a full-coverage appliance or any other type of orthodontic appliance.

Figure 7C:
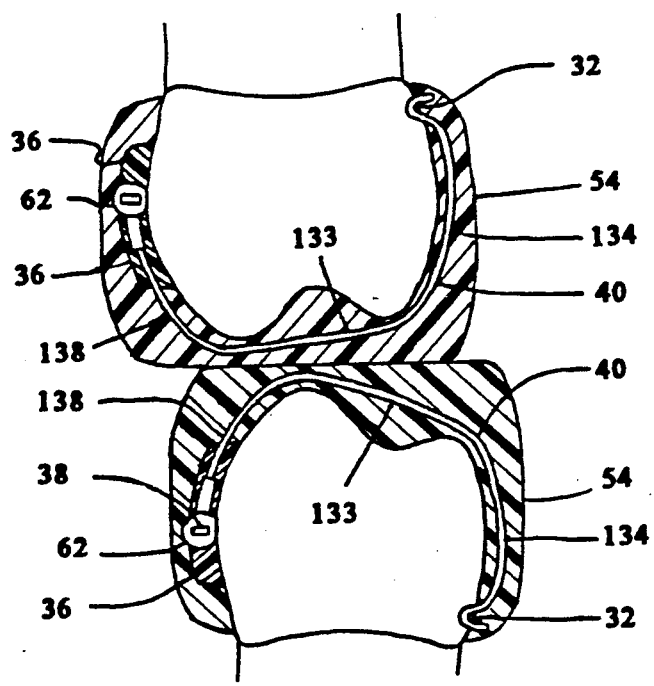
FIG. 7C is a view showing casings generally in accordance with FIG. 7A applied to both the upper and lower arch.

FIG. 7C illustrates two full coverage appliances, one covering the upper teeth and the other covering the lower teeth as in FIG. 7A.

Figure 7D:
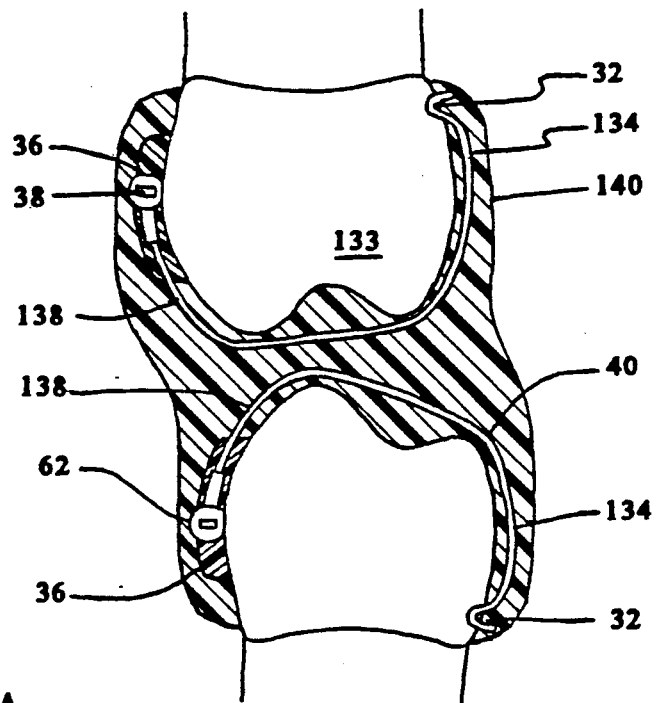
FIG. 7D is a view showing a unitary appliance covering the structure of FIG. 7 applied to both arches.

FIG. 7D is a cross-section view of a single-piece (unitary) orthodontic positioner somewhat similar to that shown by Kesling, with a molded flexible appliance 140 extending over both the upper and lower arches but containing the elements shown in FIGS. 7 to 7C, inclusive.

Figure 9:
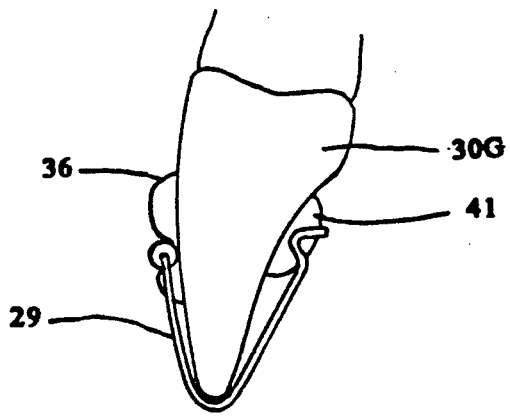
FIG. 9 is a side elevational view showing the clasp of FIG. 8 applied to an upper incisor.

FIG. 9 is a side view of an upper incisor tooth 30g having on its facial surface a button 36 having horizontal rectangular slot 47 formed therein. A second button 41 is bonded to the lingual surface of the tooth to assist in securing the Adams clasp 29 thereto.

FIG. 10 is an occlusal view of incisor 30g showing an alternate placement location for the two lingual buttons 42.

FIG. 11 illustrates the clasp assembly formed with wrought wire U-shaped spring element 43 which goes over the occlusal surface of the tooth. On the facial side is vertical stretch 44 which may be used to engage a vertical slot 48a in button 48. (See FIG. 12) Horizontal wire element 45 fixed firmly to the vertical end of the U-shaped spring element 43 is formed with curved ends 141 to engage the natural undercuts of a tooth. The elements 43 and 45 may be secured together by welding, soldering or insertion into Tee-shaped tubes (not shown) or by any other suitable means. Preferably, there is also a horizontal element 46 having inward curved ends 142 to engage the natural undercuts on the lingual side of the tooth. Element 46 may be secured to the lower end of vertical piece 143. Tube 147 secures stretch 143 to the stretch 144 of spring element 43.

FIG. 11A shows a modified clasp especially useful in treatment of rotated teeth. A clasp such as that of FIG. 11 does not properly engage such a tooth. Hence a cross 201 connector is attached to element 43. Vertical member 202 extends downward from cross 201 and is connected to inverted Tee 62, from which extend wires 141. Inverted L-shaped members 203 are connected to the other branches of cross 201 and engage the sides of button 48. FIG. 14A illustrates the clasp of FIG. 11A in place.

FIG. 12A shows an alternative button shape with the vertical slot widened and rounded at the top 48b to help guide the vertical stretch 44 of the spring element 43 into place.

FIG. 12B shows another alternative button shape with the outer contours of the button rounded at the top 48c as well as the slot widened and rounded at the top 48b.

Figure 13:
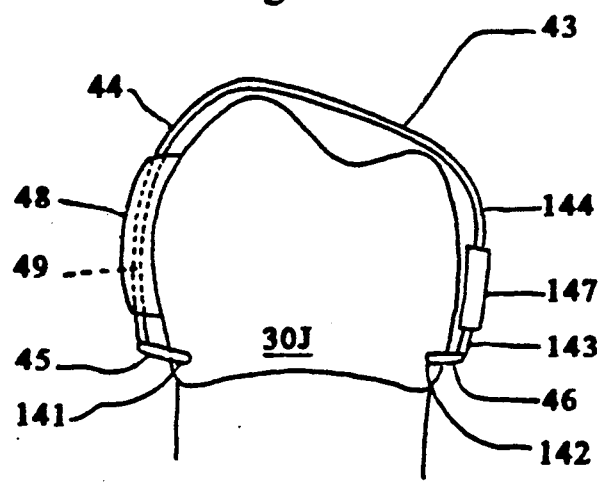
FIG. 13 is a side elevational view of a tooth to which the button of FIG. 12 and the clasp of FIG. 11 have been applied.

FIGS. 13 and 14 show the structure of FIGS. 11 and 12 applied to tooth 30j. Button 48 with a vertical slot 48a (indicated by dotted lines in FIGS. 13, 13A-3D is bonded to the facial side of the tooth 30j to receive the vertical portion 44 of spring element 43, while the ends 141 and 142 engage the undercuts of the tooth.

FIGS. 13A through 13D show application of the structure of the appliance of FIG. 13 to full-coverage and partial-coverage appliances, to full-coverage appliances and a unitary two-arch appliance, respectively.

Figure 13A:
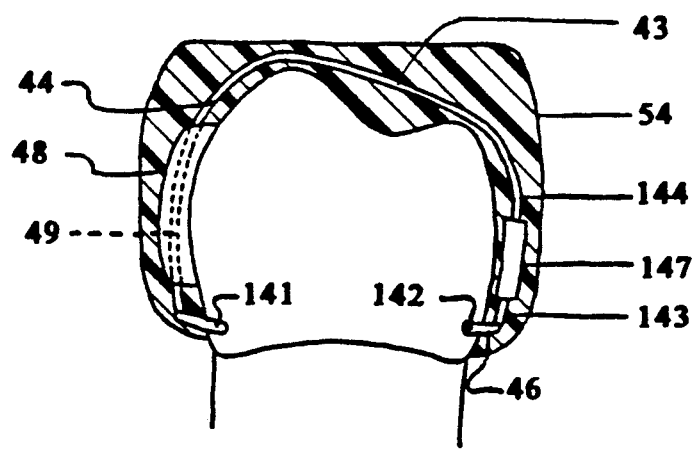
FIGS. 13A, 13B, 13C and 13D are views similar to FIGS. 7A, 7B, 7C and 7D showing use of the clasp of FIG. 13.
Figure 13B:
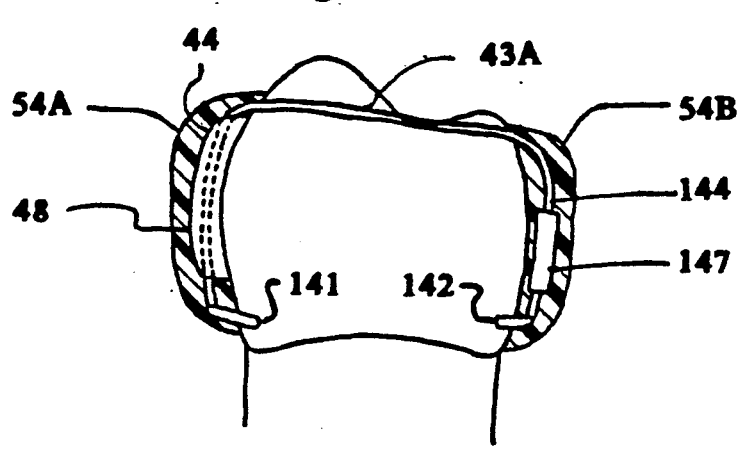
Figure 13C:
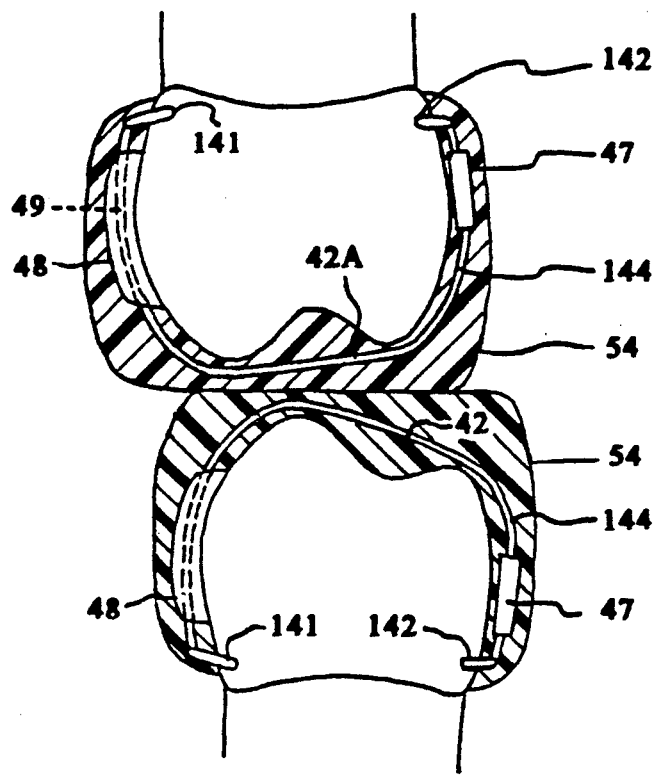
Figure 13D:
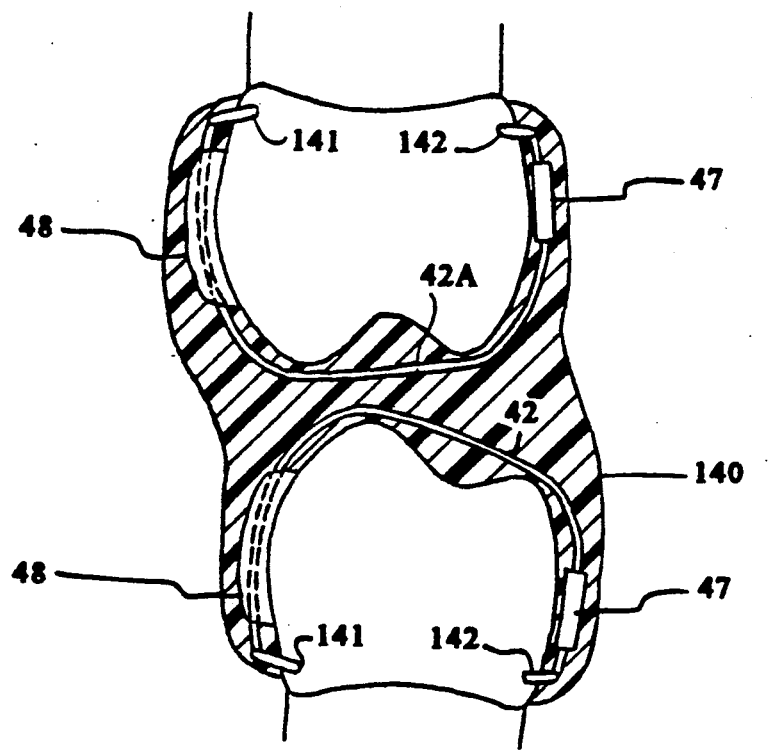

FIGS. 13A and 13C are the same and are full coverage appliances.

Figure 15:
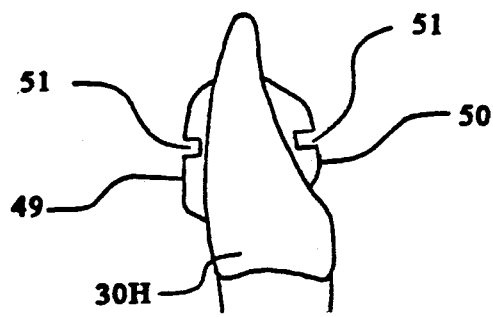
FIG. 15 is a side view of a lower central incisor with bonded buttons on both the facial and lingual surfaces.
Figure 16A:
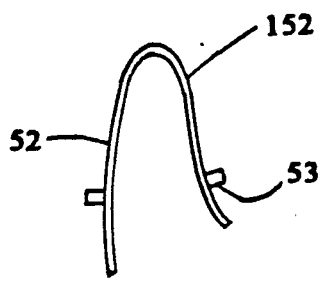
FIG. 16A is a side elevational view of the structure of FIG. 16.
Figure 16:
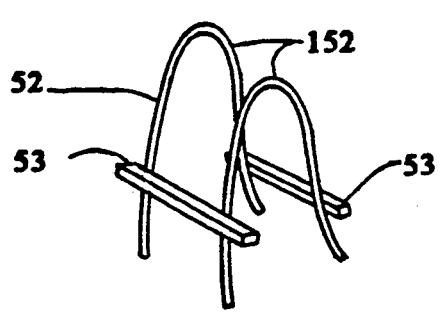
FIG. 16 is a perspective view of a clasp used with the buttons of FIG. 15.

In the modification of the invention shown in FIG. 15, a button 49 is bonded on the facial surface and a button 50 is bonded on the lingual surface of lower central incisor 30h. Each button 49, 50 has a single horizontal slot 51 approximately in its middle. The clasp 52, shown particularly in FIG. 16 and 16A, has a pair of inverted U-shaped wire elements 152 which fit over the incisal edges of the tooth and extend vertically along either side of the bonded buttons. Horizontal connector elements 53 on the facial and lingual sides interconnect and extend slightly beyond the elements 152. The connector elements 53 fit into the slots 51 as shown in FIG. 17.

Figure 17:
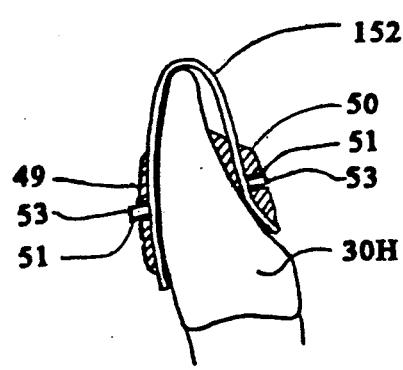
FIG. 17 is a side elevational view of the structure of FIG. 15 with the clasp of FIG. 16 applied thereto
Figure 17A:
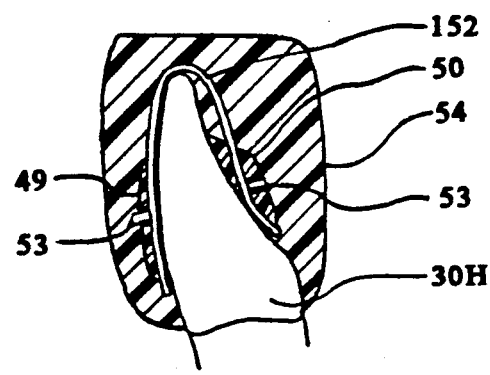
FIGS. 17A, 17B, 17C and 17D are views similar to FIG. 7A, B, C and D of the modification of FIG. 17.

FIG. 17A shows the clip-end clasps of FIG. 17 molded within a full-coverage flexible appliance.

Figure 17B:
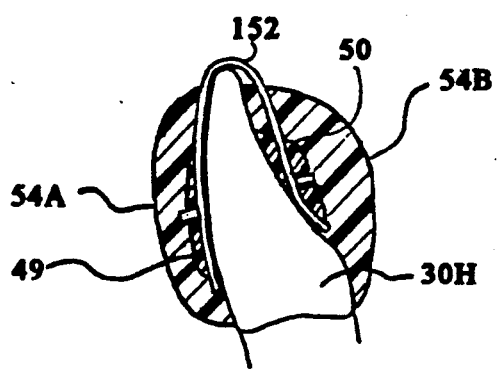

FIG. 17B shows the same clasp molded within a partial-coverage apparatus or appliance comprising members 54a and 54b on the facial and lingual sides, respectively.

Figure 17C:
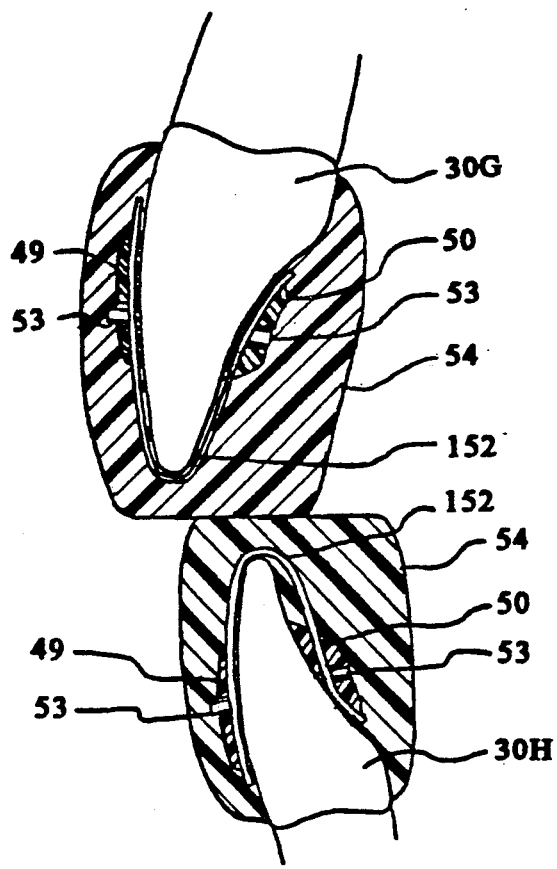

FIG. 17C shows substantially identical apparatus to that shown in FIG. 17A applied both to the upper and lower incisors 30g and 30h, respectively, as in the manner of FIG. 7C.

Figure 17D:
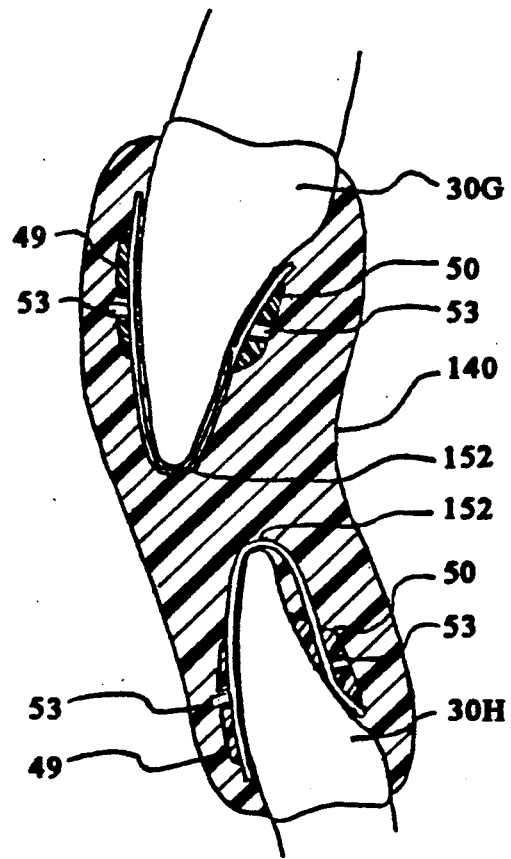

FIG. 17D is similar to FIG. 7D showing a single appliance for both arches.

Figure 18:
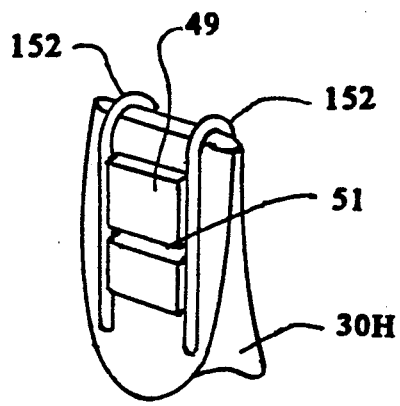
FIG. 18 is a perspective view of a lower incisor as shown in FIGS. 15-17 showing a modified construction.

FIG. 18 is a schematic perspective view of the incisor 30h showing that the spring elements 152 pass on either side of the button 49. The horizontal connector wire 53 which fits in slot 51 is omitted in this view.

Figure 18A:
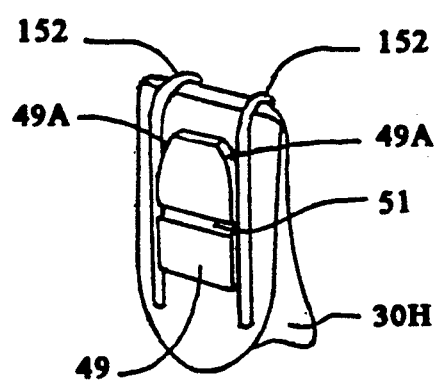
FIG. 18A is a perspective view of the same tooth as that illustrated in FIG. 18 illustrating another button shape.

FIG. 18A shows button 49a, which is a modification of button 49 of FIG. 18, with rounded, tapered sides near the top to help guide the vertical spring elements 152 to their proper place along the sides of button 49.

Figure 19:
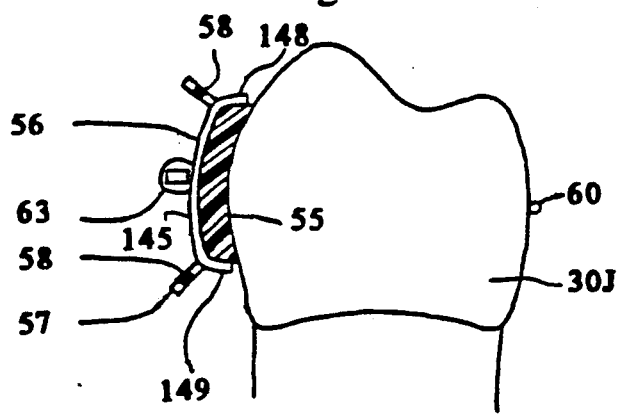
FIG. 19 is a cross-sectional view of a lower premolar showing a modified construction.
Figure 22:
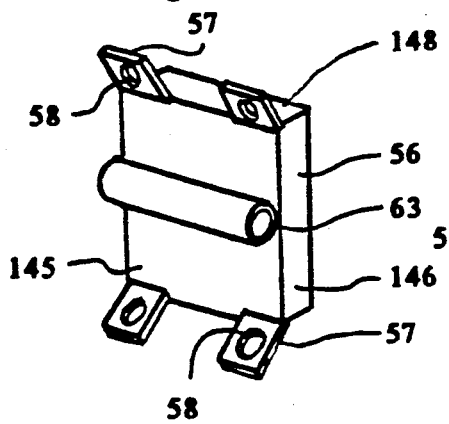
FIG. 22 is a perspective view of a cap designed to fit over a button as used in the structure of FIG. 19.
Figure 23:
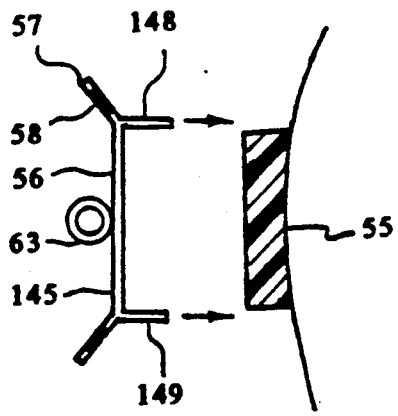
FIG. 23 is an exploded view showing the manner in which the cap fits over a button.
Figure 24:
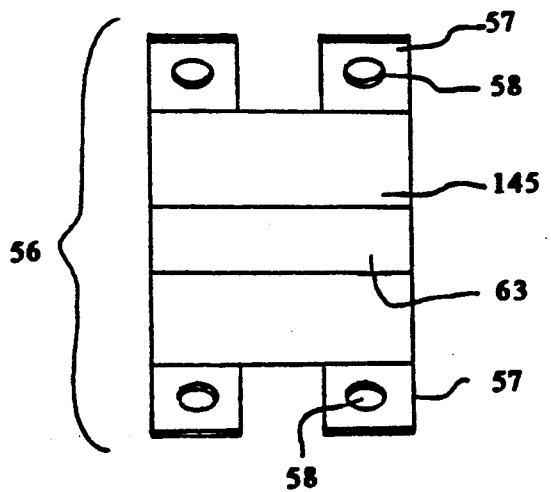
FIG. 24 is an elevational view of the button of FIG. 22.

In the modification of FIG. 19 (taken substantially along the line 19A—19A of FIG. 21) button 55 is bonded to the facial surface of pre-molar tooth 30j. In this modification, a cap 56 is used formed of plastic or metal to fit precisely over button 55. Details of the cap are shown in FIGS. 22-24. Tabs 57 formed with apertures 58 protrude outwardly from cap 56 at an angle of approximately 45 degrees to the horizontal. Lingual archwire 60 contacts the lingual surface of pre-molar 30j. Tube 63 is attached to the exterior of the center of the cap 56 and extends substantially horizontally. The interior of tube 63 may be shaped to fit either a rectangular or a round archwire 59. As shown in detail in FIGS. 22-24, the cap 56 has a front 145, opposed sides 146 and opposed top and bottom 148, 149 positioned and dimensioned to fit precisely over the button 55.

Figure 19A:
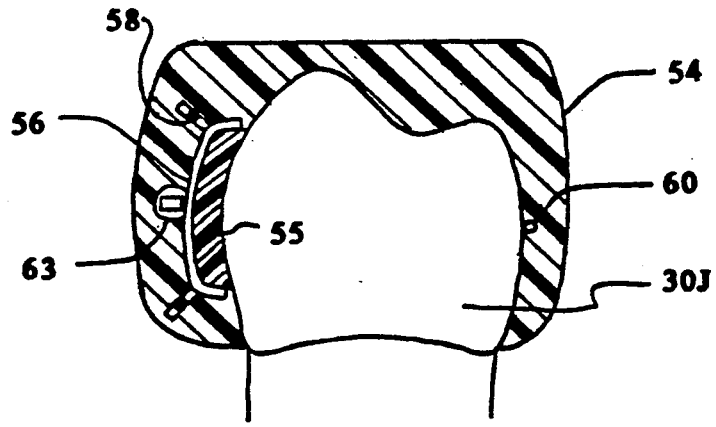
FIGS. 19A, 19B, 19C and 19D are views similar to FIGS. 7A, B, C and D of the structure of FIG. 19.
Figure 19B:
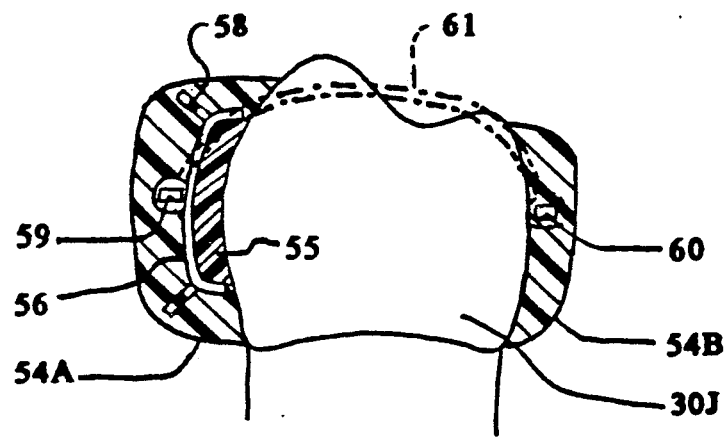
Figure 19C:
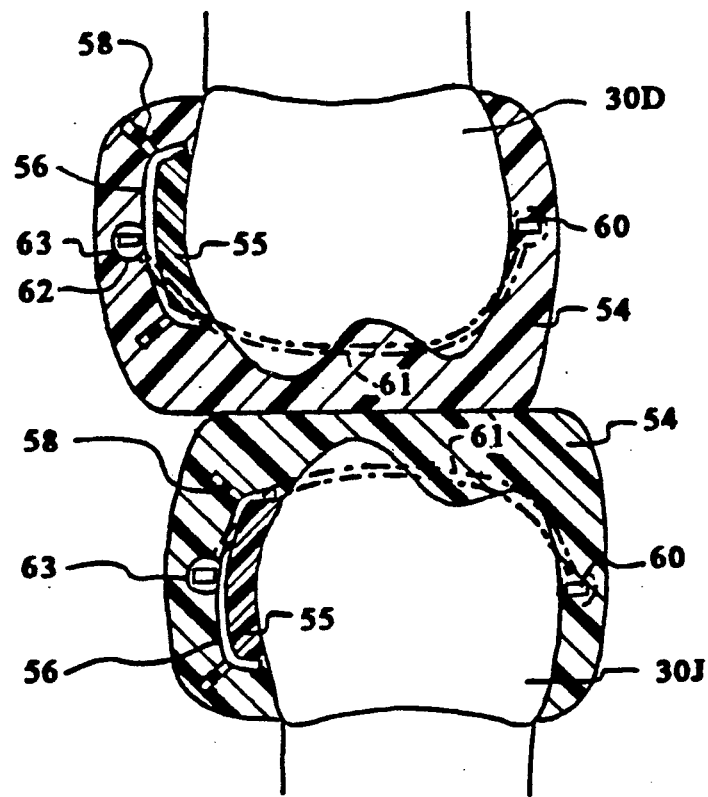
Figure 19D:
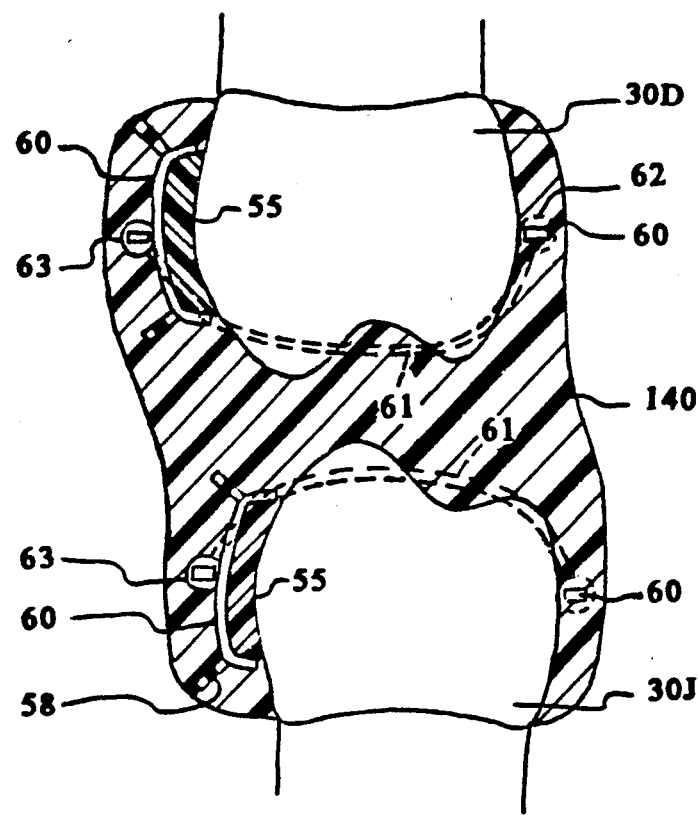

FIG. 19A shows the cap and button of FIG. 19 encased in a full-coverage molded flexible material forming an appliance 54. FIG. 19A is a cross-section view taken along line 19A—19A of FIG. 21 and also of FIG. 35. FIGS. 19A, 19C, and 19D are all taken along line 19A—19A of FIGS. 21 and 35. The U-shaped spring element 61 is not in the plane of the cross-section and is shown with a dotted outline. FIG. 19B is taken along line 19B—19B of FIG. 34. Again the U-shaped spring elements are not in the plane of the cross-section but are shown with a dotted outline. FIG. 19B shows the same cap and button enclosed within a partial-coverage apparatus having facial and lingual flexible appliance parts 54a and 54b, respectively. FIG. 19C shows an apparatus according to FIG. 19A installed on lower pre-molar 30j and a similar apparatus installed on the upper pre-molar 30d. FIG. 19D, in a manner similar to FIG. 7D, shows a single flexible apparatus for both arches.

Figure 19E:
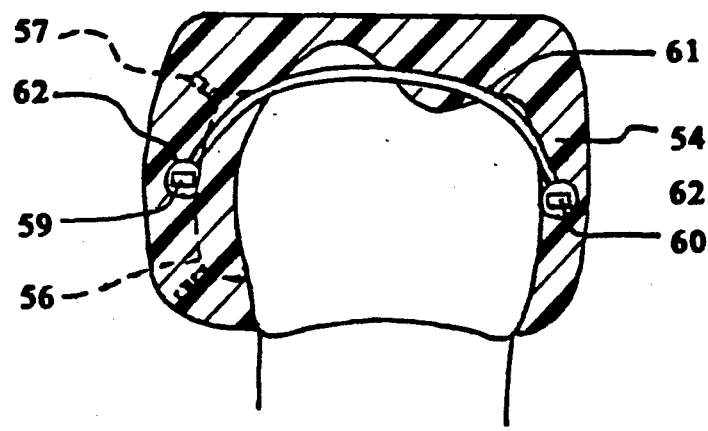
FIG. 19E is a view similar to FIG. 19A taken at a different location.
Figure 20:
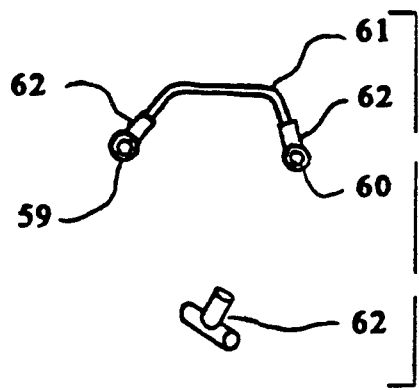
FIG. 20 is an exploded view of one of the components of the appliance shown in FIG. 19.
Figure 21:
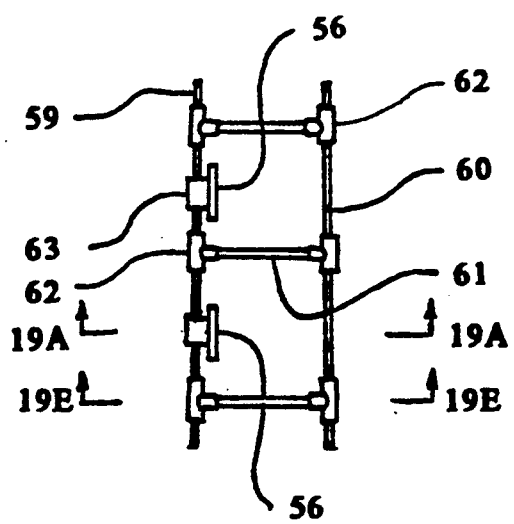
FIG. 21 is a top occlusal view of a portion of the skeleton of the appliance shown in FIG. 19.

FIG. 19E is taken along line 19E—19E of FIG. 21. The button 55 is completely hidden by the cap 56 which is shown with a dotted outline.

FIG. 21 is a top occlusal view of a portion of the skeleton of the appliance of FIG. 19. U-shaped spring elements 61 are connected to the archwires 59 and 60 by Tee-shaped connectors 62. The U-shaped spring elements 61 are designed to be positioned between teeth to provide tension on the reinforcing archwires 59 and 60. The U-shaped spring elements 61 are shown connecting the facial reinforcing archwire 59 and lingual reinforcing archwire 60. The caps 56 which cover over the buttons 55 (not shown) have tubes 63 receiving the facial reinforcing archwires 59 and 60. As shown in FIG. 21, the caps 56 are shown only on the facial sides of the teeth, but it will be understood that they may be placed either on the facial or lingual sides or both.

Figure 25:
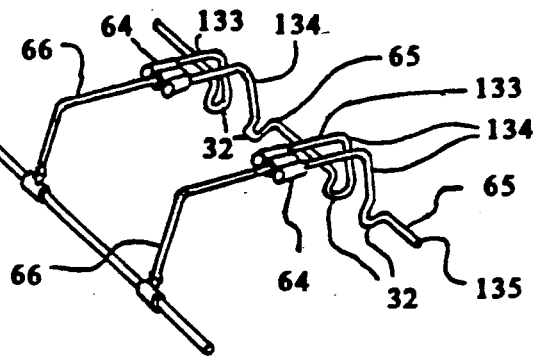
FIG. 25 is a portion of another clasp assembly.
Figure 26:
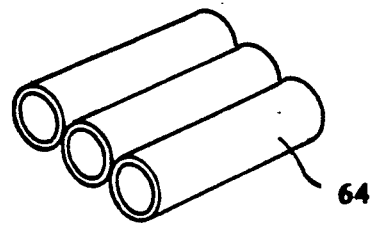
FIG. 26 is an enlarged perspective view of one of the elements of FIG. 25.

FIG. 25 shows a clasp assembly with an Adams clasp 65 on each tooth on the lingual side thereof attached to a single interproximal connector wire 66 on the facial side. The connection is accomplished by triple tube connector 64 comprising three short pieces of crimpable tubing shown in FIG. 26. Two of the pieces of tubing receive the ends of horizontal stretches 133 of the adjacent Adams clamps 65, while the other piece of tubing receives the end of the connector wire 66.

Figure 27:
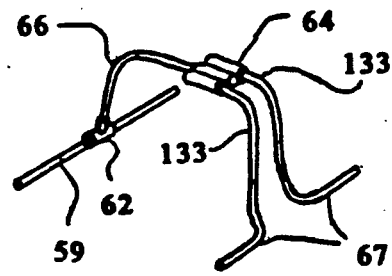
FIG. 27 is a perspective view of a further modified clasp.
Figure 28:
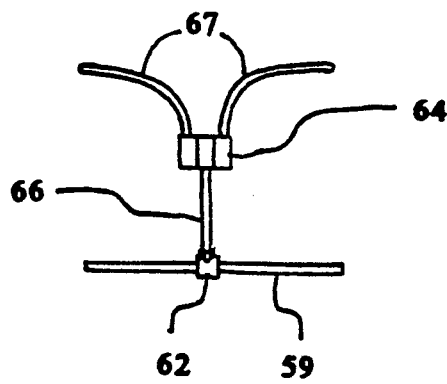
FIG. 28 is a top view of the clasp of FIG. 27.

FIG. 27 shows a different clasp receiving a single interproximal wire 66 on the facial side which has a crimpable T-shaped tube 62 to receive reinforcing archwire 59 (as in FIG. 25) but also has a triple tube section crimpable connector 64 receiving two short wire clasp sections 67 on the lingual side which can engage natural undercuts or engage under a bonded projection to provide an undercut where the natural undercut is inadequate. As best shown in FIG. 28, the single interproximal connector wire 66 attaches to the facial side archwire 39 by means of connector 62. Triple tube section connector 64 is shown positioned over the marginal ridges between the teeth. The connector 64 may also be located in a vertical position between the teeth on the lingual side so that there need be only a single interproximal connector wire 66 going over the biting surfaces of the teeth, thereby reducing the bulkiness of the appliance in that area.

Figure 30:
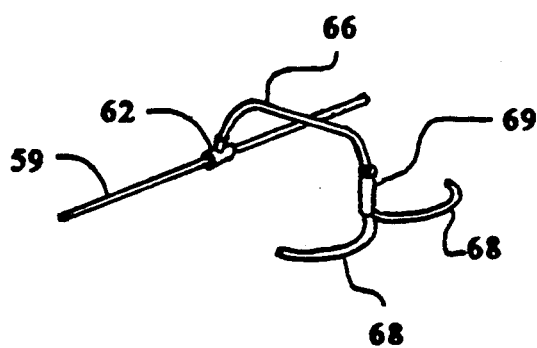
FIG. 30 is a perspective view from the lingual aspect of the clasp of FIG. 29.
Figure 29:
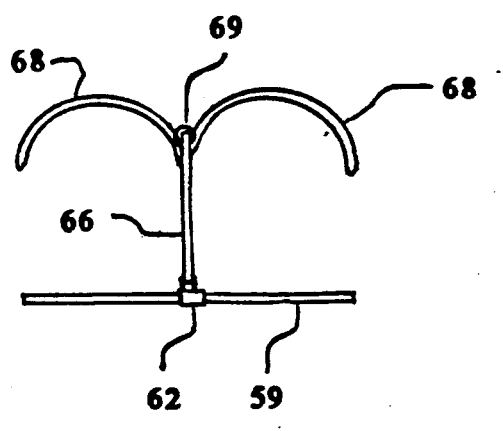
FIG. 29 is a top view of a further modified clasp.
Figure 31:
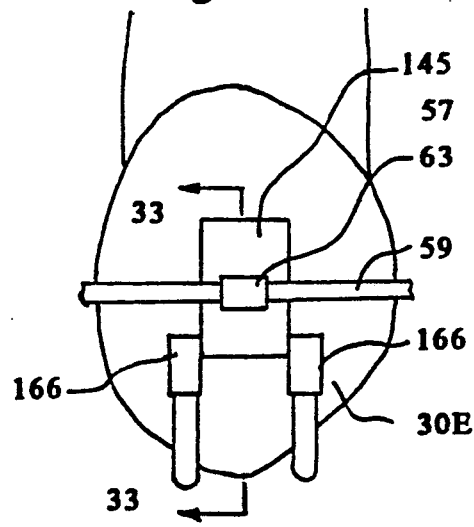
FIG. 31 is a side elevational view of a still further modified clasp.
Figure 29A:
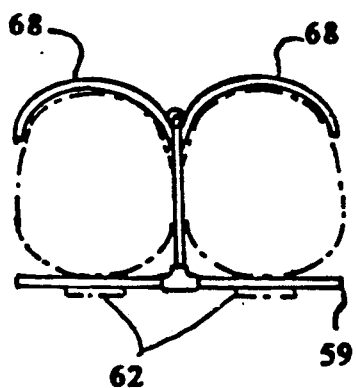
FIG. 29A shows the clasp applied to two adjacent teeth.
Figure 32:
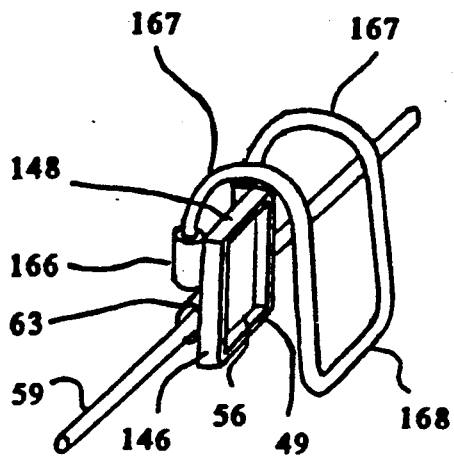
FIG. 32 is a perspective view of the clasp of FIG. 32 inverted.
Figure 33:
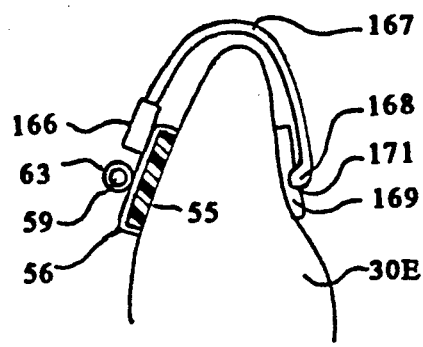
FIG. 33 is an inverted side elevational view taken substantially along the line 33—33 of FIG. 31.

FIG. 29 is a top view of another clasp variation similar to that shown in FIGS. 27 and 28. This variation shows a facial surface archwire 59 and a single U-shaped spring element 66 attached thereto by means of a crimpable tubing connector 62. On the lingual side there is a single wire 68 bent to extend below the two undercuts of two adjacent teeth and to act as a clasp. There is a vertical crimpable tube 69 welded or soldered to the lingual clasp to which U-shaped spring element 66 is attached. The variation shown in FIGS. 29 and 30 would best be shown in the bicuspid region of the mouth, a location where Adams clasps might be too bulky.

The components may be assembled shown in FIGS. 31-35 in a dental laboratory. Thus, a button 55 adheres to the facial surface of tooth 30e, here shown to be an upper cuspid. The clasp comprises a cap 56 shaped to fit over the button 55 which has a tube 63 disposed horizontally on the outer face thereof to receive facial archwire 59. Secured to cap 56 on opposite sides are crimpable tube sections 166 which receive ends of inverted U-shaped spring wire elements 167 which pass over the occlusal surfaces of the tooth 30e or to either side thereof and are joined on the lingual side by horizontal connection 168. A second button 169 may be adhered to the lingual surface of tooth 30e having a horizontal slot 171 which receives the connection 168.

Figure 36:
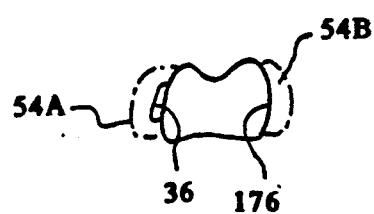
FIG. 36 is a sectional view taken substantially along the line 36—36 of FIG. 34.

In the foregoing description of the invention, reference has been made to partial-coverage and total-coverage appliances which expose the occlusal tooth surfaces or cover the same respectively. A set of partial-coverage appliances is shown on FIGS. 34 and 36. Thus the facial side 54a fits around the outside of the arch while the lingual appliance 54b is on the opposite side. These members 54a and 54b are formed with recesses 176 which are shaped to fit over the respective teeth (as well as the various buttons and clasps of the preceding modifications). The bonded buttons on the facial and lingual sides may be moved closer to the gingiva in deep overbite cases, as shown by the arrow in FIG. 37.

Figure 35:
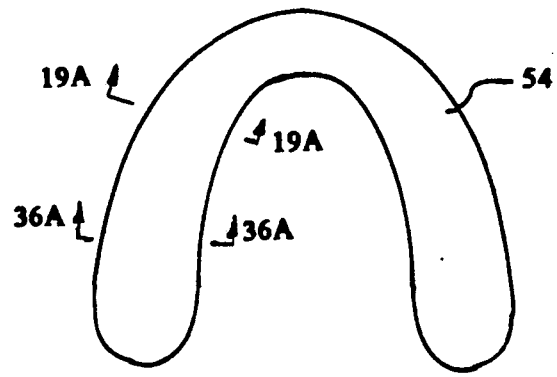
FIG. 35 is a view similar to FIG. 34 of a full coverage appliance.
Figure 36A:
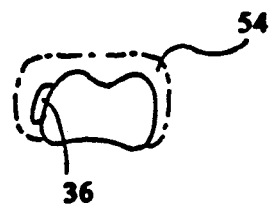
FIG. 36A is a view similar to FIG. 36 taken along the line 36A—36A of FIG. 35.

FIGS. 35 and 36A illustrate a total-coverage appliance with no exposure of the occlusal tooth surfaces.

Figure 37:
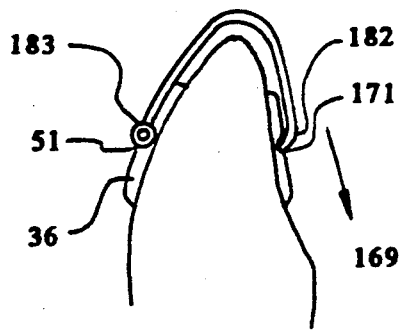
FIG. 37 is a side elevational view of a further modified clasp showing use of buttons on both the facial and lingual sides of an incisor.
Figure 38:
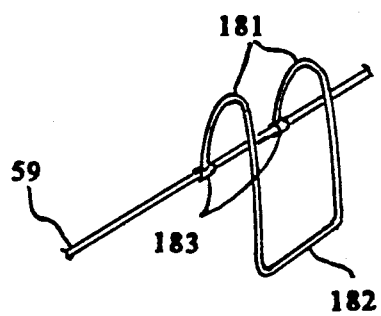
FIG. 38 is a perspective view of a clasp used in the structure of FIG. 37.

FIGS. 37 and 38 illustrate another type of clasp comprising inverted U-shaped elements 181, the lingual ends thereof being interconnected by horizontal connection 182. Crimpable short tube sections 183 are secured to the facial ends of the elements 181 to receive a facial horizontal archwire 59. Facial button 36 is formed with a horizontal slot 51 to receive said horizontal archwire 59 secured by tube sections 183. A lingual button 169 formed with a horizontal slot 171 receives the horizontal connection 182. It will be understood that connections 183 may be T-shaped, if desired.

Figure 39:
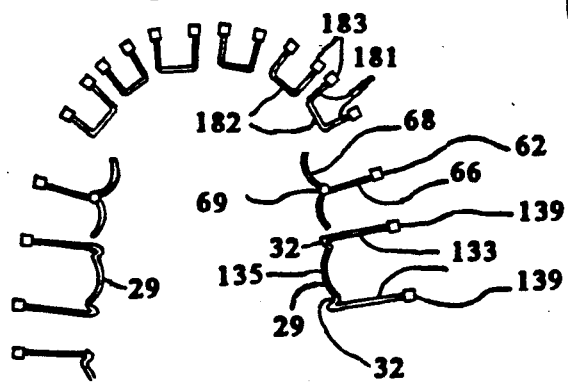
FIG. 39 is a schematic top view showing an arrangement of clasps as they would be applied to a dental arch.

FIG. 39 illustrates schematically how various clips of the type shown in FIGS. 37 and 38 as well as others may be arranged around a dental arch. In the center of the figure are six clasps similar to those shown in FIGS. 37-38 to fit into facial side surface buttons on all teeth. Interproximal clasps similar to that shown in FIG. 29 may be used between bicuspids and Adams clasps having ears 32 may be used on the first molars. In all these instances, the linguals of the anterior teeth are provided with bonded buttons to receive the clasps.

Figure 40:
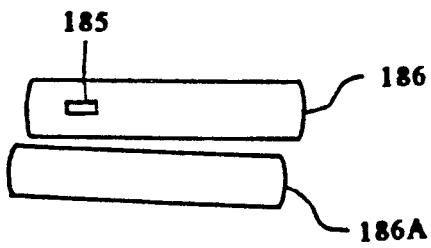
FIG. 40 is a side elevation of two single arch full-coverage positioner appliances of the type shown in FIG. 35.
Figure 40A:
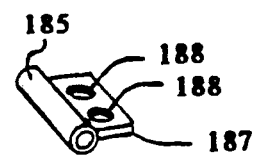
FIG. 40A is an enlarged perspective view of a headgear tube.

Directing attention to FIG. 40, upper 186 and lower 186a single arch full-coverage appliances of the type shown in FIG. 35 are installed on the lower and upper arches respectively. The appliances are shown in approximately the natural position with the patient's mouth slightly open in a relaxed posture. The internal details of the clasp assemblies are not shown, but they may be any of the types heretofore described. A headgear tube 185 is shown positioned along the side of the upper positioner 186 near the upper first molar. Headgears have been used on positioners for a considerable time and hence are not shown in the accompanying drawings. A tube 185 is shown in detail in FIG. 40A comprising a flat tab 187 attached along the side of the headgear tube to be inserted into the body of the positioner. The tab 187 is formed with holes 188 through which the molded flexible material which forms the body of the appliance may flow to fixedly attach the headgear tube to the body of the appliance. It will be understood that other ways of attaching a headgear tube to positioners in accordance with the present invention may be employed. Thus, the headgear tube 185 may be attached to internal archwires to clasp elements or to other strong internal elements to ensure that the headgear tube does not tear away from the body of the positioner. FIGS. 40 and 40A are intended to illustrate that headgears can be used in connection with the positioners heretofore described.

Figure 41:
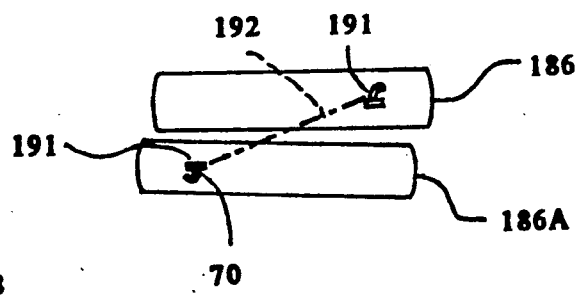
FIG. 41 is a side elevational view of two single arch full-coverage positioners of the type shown in FIG. 35 illustrating the use of a rubber band interconnecting hooks on the upper and lower dental arches.

FIG. 41 illustrates upper 186 and lower 186a single-arch, full-coverage positioner appliances of the type shown in FIG. 35 containing clasps similar to those described throughout the body of this specification. Hooks 191 for rubber bands of the type commonly used in orthodontics are shown on both appliances. In the Kurz reference, previously mentioned, elastics are used only in a vertical direction and specially shaped guideways provide for orientation of the positioners. In the present invention, rubber bands 192 interconnecting the two hooks 191 and extending in any direction apply force to the appliances. The hooks 191 may be located wherever they are needed to reposition teeth of a particular patient. The means whereby the hooks 191 are connected to the molded appliance material may be with a flat tab similar to that shown in FIG. 40A or some other attachment means.

FIG. 42 again shows upper 186 and lower 186a single-arch, full-coverage positioner appliances of the type shown in FIG. 35. These positioners are illustrated in approximately the natural position they would assume if the patient wearing them had his mouth slightly opened in a relaxed posture. As will be understood, the internal details of the clasp assemblies are not shown but they may be any of those previously described. Rigid connecting posts 196, 197 for the upper and lower appliances 186, 186a, respectively, are used. Upper post 196 is positioned approximately opposite the upper first molar. Lower connecting post 197 is preferably located approximately opposite the lower cuspid. Again, the means for attaching the posts to the body of the positioner may vary depending on the internal reinforcing structure and individual clasp design chosen for a particular case to be treated, but it will be understood that they should be attached to a fairly substantial element within the body of the positioner or to an archwire to avoid tearing the connecting posts out of the molded intermediate material that forms the body of the positioner. A commercially available Herbst appliance uses a set of two telescoping arms 198, 199 one on each side of the mouth swivel on posts 196, 197 to position the patient's lower jaw forward of the natural rest position. Thus, the Herbst type of appliance may be used in connection with the positioners of the present invention, if desired.

The arms 198, 199 are attached to the connecting posts 196, 197 in such manner that they may swivel or rotate around the long axis of the connecting posts. The length of rod 199 is determined to hold the patient's incisor teeth in approximately an edge-to-edge position. So long as the rod 199 is inserted in the tube 198, the patient's lower jaw is held in a forwardly protruding position. If the patient opens his jaws wide and removes rods 199 from tube 198 and returns the jaw to normal rest position, each end of the telescoping arm assembly swivels about the corresponding connecting post out of the patient's way. This is desirable while eating. It will be understood that the appliances 186, 186a may also be removed for such purpose (except for the buttons which are bonded to the teeth).

FIGS. 43 and 43A show use of the appliances 186, 186a with the so-called "Jasper jumper". In FIG. 43 the appliances 186, 186a are in approximately the natural position they would assume if the patient wearing them had his mouth slightly opened in a relaxed posture. The internal details of the clasp assemblies are not shown, but it will be understood that they may be any of those previously discussed. A headgear tube 185 is shown positioned along the side of the upper positioner near the upper first molar tooth. Pin 75 having a spherical ball 75a on one end is inserted through the upper hole 77 at the end of a Jasper jumper appliance and a pin 75 retains the appliance to the headgear tube because it is bent over at its end. The Jasper jumper appliance 74 is attached by a heavy wire loop 73 built into positioner 186a which extends outward from the body of the single-arch positioner appliance 186. Jasper jumper 74 slides along loop 73 to permit the patient to open and close his jaws. The lower end of the Jasper jumper appliance is free to slide a short distance forward and backward along the heavy wire loop 73 which is attached to the lower positioner 186a. The use of Jasper jumpers is well understood in the orthodontics profession.

Figure 45:
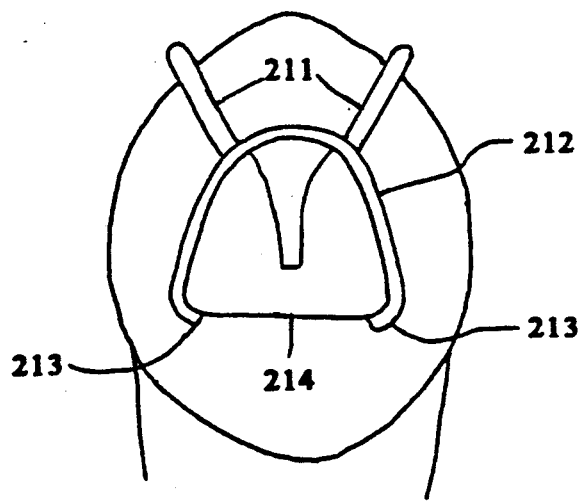
FIG. 45 is a view similar to FIG. 44 showing a clasp assembly in place.
Figure 46:
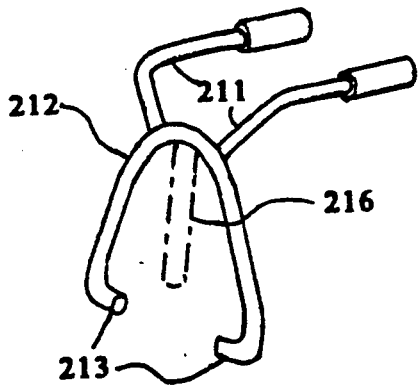
FIG. 46 is a perspective view of the clasp of FIG. 45.

FIGS. 44–46 show a further modified button 206 on tooth 30j and a modified clasp. Button 206 has upwardly-inwardly curved flanks 207. Slot 208 has outwardly-upwardly curved side edges 209. The wires 211 are attached by any convenient means to wire 212 which is complementary to the shape of the side edges of button 206 and has terminal inwardly turned ends 213 which engage under the bottom edge 214 of button 206 to hold the clasp in place. Optimally, as shown in FIG. 46 vertical guide wire 216 may be positioned to fit into slot 208.

Figure 47:
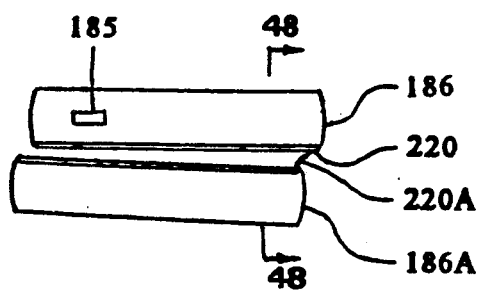
FIG. 47 is a front elevational view of modified upper and lower full coverage appliances.
Figure 48:
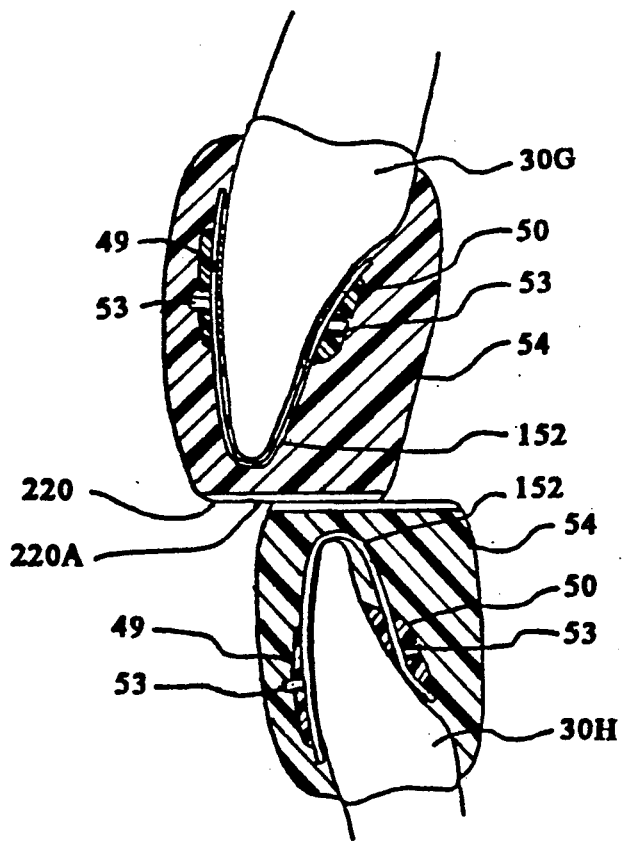
FIG. 48 is a vertical sectional view along line 48—48 of FIG. 47.

Directing attention to FIGS. 47–48, the occlusal surfaces 220, 220A are made of a more rigid plastic material than the body. As explained in U.S. Pat. No. 4,793,803, the resilient body 54 tends to pull the teeth 30G and 30H into proper position.

For convenience, the terms "upward" and "downward" are used in the appended claims in the sense that the appliance is installed on the lower arch of the patient. When the appliance is installed on the upper arch, these terms have the opposite meaning.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. In an orthodontic appliance,
at least one clasp formed of spring wire comprising, in order, engagement means to engage a first surface of a tooth formed with an undercut, an upward extending first generally vertical stretch, a generally horizontal stretch across the occlusal surface of said tooth and a downward extending second generally vertical stretch and first attachment means on a second surface of said tooth opposite said first surface, said engagement means comprising a bent wire ear shaped to engage said undercut,
a button adhered to said second surface of said tooth, said button being formed with second attachment means to detachably engage said first attachment means,
said first attachment means further comprising means to receive archwire.

2. An appliance according to claim 1 which further comprises a plastic appliance molded to conform to at least one arch of the patient's jaw encasing at least a substantial portion of said clasp.

3. An appliance according to claim 2 in which said appliance encases the occlusal surfaces of said arch and the entirety of said clasp.

4. An appliance according to claim 2 in which said appliance comprises a first member encasing said engagement means and said first vertical stretch and a second member encasing said second vertical stretch and said first attachment means, the occlusal surface of said arch and a substantial portion of said horizontal stretch being uncovered.

5. An appliance according to claim 2 which further comprises a second clasp similar to said first-mentioned clasp on the arch of the patient opposite said first-mentioned arch, said plastic appliance encasing both said first-mentioned clasp and said second clasp.

6. An appliance according to claim 1 in which said wire clasp further comprises a second engagement means engaging said first surface spaced laterally from said first engagement means, a generally horizontal connection between said first and second engagement means on said first surface, an upward extending third vertical stretch, a second generally horizontal stretch across the occlusal surface of said tooth spaced laterally from said first-mentioned horizontal stretch, a downward extending fourth generally vertical stretch, and a third attachment means on said second surface,
said button being formed with fourth attachment means to detachably engage said third attachment means.

7. An appliance according to claim 6 in which both said second and third attachment means each further comprises means to receive an archwire.

8. An attachment according to claim 6 in which said third engagement means comprising an ear to engage said undercut.

9. An attachment according to claim 1 which further comprises a second button on said first surface formed with second engagement means to engage said first-mentioned engagement means.

10. An appliance according to claim 1 in which said first vertical stretch comprises two discrete aligned sections and which further comprises a crimp tube receiving and crimped to said aligned sections.

11. An appliance according to claim 1 in which said first attachment means further comprises a second horizontal stretch adjacent the gingival area of the second surface of said tooth located below said button and extending in opposite directions from said second vertical stretch, the opposite ends of said second horizontal stretch being formed with hooks to engage said tooth on opposite sides of said second surface.

12. An appliance according to claim 11 in which said button is formed with a vertical groove to receive said second vertical stretch.

13. An appliance according to claim 1 which further comprises an upward extending third generally vertical stretch, a second generally horizontal stretch across the occlusal surface of said tooth and a downward extending fourth vertical stretch, said engagement means extending generally horizontally and attached to said first and third vertical stretches and engaging said first surface, said first attachment means extending generally horizontally and attached to said second and fourth vertical stretches,
   said first attachment means further comprising a cap shaped to fit over and around the sides of said button.

14. An appliance according to claim 13 in which said cap further comprises outwardly angled tabs.

15. An appliance according to claim 14 which further comprises a plastic appliance molded to conform to at least one arch of the patient's jaw encasing a substantial portion of said clasps, said tabs augmenting adherence of said clasps to said appliance.

16. An appliance according to claim 15 in which said first attachment means further comprises generally vertical short sockets adjacent opposite sides of said cap receiving the lower ends of said second and fourth vertical stretches.

17. An appliance according to claim 16 in which said first attachment means further comprises a horizontal tab attached to said cap shaped to receive an archwire.

18. An appliance according to claim 13 which further comprises a second button attached to the lingual surface of said tooth formed with a slot to receive said engagement means.

19. An appliance according to claim 1 to fit said first-mentioned tooth and an adjacent second tooth comprising a second wire clasp, said second clasp comprising second engagement means to engage a first surface of said second tooth, an upward extending third generally vertical stretch, a second generally horizontal stretch across the occlusal surface of said second tooth,
   a second button adhered to the second surface of said second tooth formed with third attachment means, said first attachment means engaging said second and third attachment means,
   a fastener receiving said first-mentioned and said second horizontal stretches,
   a common wire member having a first end received in said fastener and extending between the occlusal surfaces of said first-mentioned and second teeth, said wire member having a second end attached to said first attachment means.

20. An appliance according to claim 19 in which said fastener comprises three parallel, short tubular sections secured together.

21. An appliance according to claim 19 in which said first-mentioned and second engagement means each comprises an ear to engage an undercut of one of said teeth.

22. An appliance according to claim 19 in which said first-mentioned and second engagement means each comprises a generally horizontal curved wire shaped to fit around the lingual surfaces of said first-mentioned and second teeth close to the gum line.

23. An appliance according to claim 1 in which said engagement means is shaped to engage a first surface of a second tooth adjacent said first-mentioned tooth, and which further comprises a second button on a second surface of said second tooth, said second button being formed with third attachment means, said first attachment means detachably engaging said third attachment means.

24. An appliance according to claim 23 in which said engagement means comprises first and second generally horizontal curved wires shaped to fit around the lingual surfaces of said first-mentioned and second teeth, respectively, close to their gum lines.

25. An appliance according to claim 23 in which said first vertical stretch is formed in two sections and which further comprises means to connect said two sections.

26. An appliance according to claim 23 in which said horizontal stretch extends between the occlusal surfaces of said first-mentioned and second teeth.

27. An attachment according to claim 1 in which said clasp further comprises an upward extending third vertical stretch on said first surface spaced laterally from said first vertical stretch, a second generally horizontal stretch extending from the upper end of said third vertical stretch across said occlusal surface, a downward extending fourth generally vertical stretch on the facial end of said second horizontal stretch,
   said engagement means interconnecting the lower ends of said first and third vertical stretches, said first attachment means engaging the lower ends of said second and fourth vertical stretches.

28. An attachment according to claim 27 which further comprises a second button on said second surface of said tooth, said engagement means engaging said second button.

29. An attachment according to claim 27 in which said first engagement means comprises short horizontal tubes on the lower ends of said second and fourth vertical structures and an archwire through said tubes, said archwire engaging said button.

30. An appliance according to claim 1 on a first arch of a patient and which further comprises a second appliance similar to said first-mentioned appliance on the second arch of the patient and biasing means to bias said appliances relative to each other, said biasing means having first and second anchoring means on said first-mentioned and second appliances and means interconnecting said first and second anchoring means.

31. An appliance according to claim 1 which further comprises a coil intermediate said first vertical stretch and said horizontal stretch.

32. An appliance according to claim 1 in which said button has side edges and said first attachment means comprises wires engaging said side edges to bias a rotated tooth toward normal position.

33. An appliance according to claim 32 in which said side edges are slanted to facilitate attachment of said appliance.

34. An appliance according to claim 32 in which said second attachment means further comprises a vertical slot in said button, said first attachment means comprising a vertical wire in said slot.

35. An appliance according to claim 34 in which said vertical slot has upwardly-outwardly diverging side edges to facilitate entry of said vertical wire into said slot.

36. An appliance according to claim 35 in which said button has rounded upper outer corners to facilitate said first attachment means engaging side edges of said button.

37. An appliance according to claim 36 in which said first attachment means has vertical wires engaging said side edges of said button.

38. An appliance according to claim 37 in which said vertical wires have inturned lower ends engaging under the bottom edge of said button.

39. An appliance according to claim 1 in which said second attachment means comprises a vertical slot, said slot having upwardly-outwardly diverging side edges to facilitate entry of said first attachment means into said slot.

40. In an orthodontic appliance,
at least one clasp comprising, in order, engagement means to engage a first surface of a tooth, an upward extending first generally vertical stretch, a generally horizontal stretch across the occlusal surface of said tooth and a downward extending second generally vertical stretch and first attachment means on a second surface of said tooth opposite said first surface,
a button adhered to said second surface of said tooth, said button being formed with second attachment means to detachably engage said first attachment means,
said engagement means comprising a second horizontal stretch adjacent the gingival area of the first surface of said tooth extending in opposite directions from said first vertical stretch, the opposite ends of said second horizontal stretch being formed with hooks to engage said tooth on opposite sides of said first surface thereof.

41. In an orthodontic appliance,
at least one clasp comprising, in order, engagement means to engage a first surface of a tooth, an upward extending first generally vertical stretch, a generally horizontal stretch across the occlusal surface of said tooth and a downward extending second generally vertical stretch and first attachment means on a second surface of said tooth opposite said first surface,
a button adhered to said second surface of said tooth, said button being formed with second attachment means to detachably engage said first attachment means,
said clasp further comprising an upward extending third generally vertical stretch, a second generally horizontal stretch across the occlusal surface of said tooth and a downward extending fourth generally vertical stretch, said engagement means extending generally horizontally and attached to said first and third vertical stretches, said first attachment means extending generally horizontally and attached to said second and fourth vertical stretches,
and which further comprises a second button adhered to said first surface, said second button being formed with third engagement means to engage said first-mentioned engagement means.

42. An appliance according to claim 41 in which said second attachment means comprises a horizontal slot to engage said first attachment means.

43. An appliance according to claim 42 in which said first attachment means comprises a horizontal wire.

44. An appliance according to claim 41 in which said third attachment means comprises a horizontal slot to engage said first engagement means.

45. An appliance according to claim 44 in which said first engagement means comprises a horizontal wire.

46. An appliance according to claim 41 in which said first-mentioned button comprises substantially parallel vertical sides, said second and fourth vertical stretches engaging said vertical sides.

* * * * *